SELF-CONTAINED INTERNAL HYDROTHERAPY APPARATUS

Original Filed March 6, 1970 6 Sheets-Sheet 1

INVENTOR.
Rose Marie Hudson

BY

Stepno & Nielsen
ATTORNEYS

SELF-CONTAINED INTERNAL HYDROTHERAPY APPARATUS

Original Filed March 6, 1970 6 Sheets-Sheet 2

INVENTOR.
Rose Marie Hudson
BY
Stepno & Neilson
ATTORNEYS

SELF-CONTAINED INTERNAL HYDROTHERAPY APPARATUS

Original Filed March 6, 1970 6 Sheets-Sheet 5

INVENTOR.
Rose Marie Hudson

BY

Stepno & Neilan
ATTORNEYS

SELF-CONTAINED INTERNAL HYDROTHERAPY APPARATUS

Original Filed March 6, 1970 6 Sheets-Sheet 4

INVENTOR.
Rose Marie Hudson

BY

Stipno & Nelson
ATTORNEYS

SELF-CONTAINED INTERNAL HYDROTHERAPY APPARATUS

Original Filed March 6, 1970 6 Sheets-Sheet 5

INVENTOR.
Rose Marie Hudson
BY
Stepno & Neilson
ATTORNEYS

SELF-CONTAINED INTERNAL HYDROTHERAPY APPARATUS

Original Filed March 6, 1970 6 Sheets-Sheet 6

INVENTOR.
Rose Marie Hudson

BY

Stipno & Yeilen
ATTORNEYS

United States Patent Office

Re. 28,130

Reissued Aug. 20, 1974

28,130

SELF-CONTAINED INTERNAL HYDROTHERAPY APPARATUS

Rose Marie Hudson, Washington, D.C., assignor to Hudall Corporation, Bethesda, Md.

Original No. 3,678,932, dated July 25, 1972, Ser. No. 17,074, Mar. 6, 1970. Application for reissue Aug. 28, 1973, Ser. No. 392,219

Int. Cl. A61m *3/00*

U.S. Cl. 128—227 10 Claims

Matter enclosed in heavy brackets [ ] appears in the original patent but forms no part of this reissue specification; matter printed in italics indicates the additions made by reissue.

ABSTRACT OF THE DISCLOSURE

A self-contained internal hydrotherapy apparatus for treatment of human patients comprising a mobile cabinet having a generally planar top surface designed to accommodate a reclining patient, a treatment system capable of infusing a desired treating solution into the body orifices and additionally externally cleansing the rectal and genital areas of the patients body, a self-contained waste disposal system, a self-contained fresh water system and an internal electrical system. The applicator elements of the treatment system are removable from the cabinet for treatment of patients confined in bed.

BACKGROUND OF THE INVENTION

The present invention relates to an internal hydrotherapy unit which is entirely self-contained and which has been designed to serve a five-fold purpose. The apparatus may be applied in the conventional manner for administration of enema therapy, or alternatively in the field of gynecological treatment for the female, for genital-urinary therapy, external lavage, and in addition may be modified for application to the newly developing field of space medicine.

The prior art is replete with various therapeutic irrigation apparatus. The various types of apparatus heretofore known in the art can generally be categorized into two distinct classes, namely those designed for permanent installation and those of a portable nature. The former class is exemplified generally by the devices disclosed in U.S. Pat. Nos. 1,758,332, 1,945,081, 2,252,569, 2,506,183 and 2,564,135 each of which is designed for permanent installation in hospitals or like institutions. Each such device is rendered highly immobile as a result of its permanent construction and necessary connection to existing plumbing and waste disposal systems. Characteristic of the latter class of treatment system are those disclosed in U.S. Pat. Nos. 1,958,100, 2,133,626, 2,176,235 and 2,852,025. Although each of these devices is portable in nature, use thereof is restricted by virtue of their dependence upon immediate proximity to existing plumbing facilities. Furthermore, all of the prior art devices suffer from the additional disadvantage that their design requires the attendance of additional personnel during the treatment of the patient, thereby removing the element of privacy from the treatment procedure. Lack of privacy can greatly impede the effectiveness of the various types of therapy involved because relaxation and comfort of the patient are considered important factors for the successful treatment of bowel impactions and other obstructions or infections in the human body, and it is most often impossible to achieve the necessary relaxed atmosphere when the patient is confronted with strangers during therapy. This problem is particularly acute in connection with the permanently installed apparatus since treatment is usually restricted to a laboratory type setting, or at least is outside the privacy of the patient's own room. But, perhaps the most severe limitation of all the heretofore known apparatus resides in their inability to effectively treat a patient who has been immobilized as, for example, by being placed in traction, or for any other reason not able to leave the confinement of bed.

It is therefore quite apparent that a new and improved apparatus for conducting the multitude of internal and external treatment procedures outlined above would be welcomed by those in the medical profession. Such a system should most desirably be mobile so as to provide treatment in any location, preferably in the privacy of a patient's room, and furthermore should be free from any restrictions involving attachment to existing plumbing or waste disposal facilities. Moreover, the ideal system would be one that the patient could control by himself without the need for extraneous personnel, and furthermore would be such that an immobilized patient could be treated within the confinement of his own bed.

SUMMARY OF THE INVENTION

It is the principal object of the present invention to provide an internal hydrotherapy apparatus which is highly mobile yet completely self-contained so as to avoid all restriction based on dependence upon existing plumbing and waste disposal facilities. In furtherance of this objective, the apparatus is to be operable within the exclusive control of the patient so that treatment may take place in complete privacy within the patient's own room.

A further but no less important object is to provide an apparatus which is not only characterized by a degree of mobility and design that enable it to be taken to any patient regardless of location, but in addition, one which will provide for treatment of those patients confined to a hospital bed.

The internal hydrotherapy apparatus of the present invention has been designed to serve a five-fold purpose which includes enema therapy, gynecological use for the female, genito-urinary, therapy, external lavage and possible modification for space medicine. As a unit for applying enema therapy, the present invention provides a natural method to remove bowel impactions or obstructions in the human body brought on by etio-logical factors involving chronic constipation, post-operative shock, administration of anesthetics, trauma and the like. The self-contained unit can be utilized at the patient's bedside for bowel cleansing, or in the case of immobility, in the bed itself. The feature of reserving exclusive control of operation to the patient serves as a time-saving and labor-saving benefit in connection with hospital personnel. Of all importance is the fact that the apparatus has been designed for the comfort, benefit, dignity and propriety of the patient providing treatment without constraint, pressure or irritation.

The therapy is based upon the principle of the enema, a gravitational flow of water, with or without medication, introduced internally via the anal opening. The present invention provides significant advantages over any known method of enema procedure primarily due to the fact that the unit is self-contained in design and allows the patient to fully control the procedure in privacy with a minimum of discomfort, thus automatically contributing to a successful therapeutic treatment. Being properly relaxed and normally positioned, the patient is able to urinate, eliminate and defecate at will in a normal and natural manner and is not forced to retain bowel content after an enormous infusion of water as is associated with the normal enema procedure. As a result of the improved physical and physiological state of the patient, the therapy is more extensive and thorough in its application because it not only gently removes bowel impactions, but it also increases the relaxation of the treated areas through increased blood circulation, and it mildly stimulates the sphincter reflex and helps to increase peristalsis. The result is a cleansing higher into the colon due to the beneficial factors inherent in the treatment concept. By contributing to the normal function of evacuation, and when proper clinical procedures are followed in administrating this therapy, the presently proposed method supercedes and is vastly superior to all past procedures in the field of clinical applications.

Moreover, this procedure may remove or minimize any upper gastro intestinal complications or side effects such as nausea, cramping, pain or flatulence sometimes accompanying the present enema procedures. The apparatus of the present invention is also capable of reducing dehydration states in the patient which contribute to impaction, congestion, low-grade infection or febrile states. The foregoing bodily conditions may be remarkably improved through treatment with the present apparatus by virtue of its ability to lower the body temperature and also to replace the water content.

The present invention also provides for a treatment of bacterial invasions of the intestinal tract since such conditions may respond very quickly to slow infusion of medication into the bowel. In addition, bowel cleansing must not be overlooked as a prerequisite to abdominal surgical procedures or obstetrical functions or procedures. The present apparatus provides for accomplishment of these procedures without dependence upon oral administration of medication which often contributes to the general condition and resistance of the patient to withstand surgical shock and/or secondary infections.

The present internal hydrotherapy apparatus is specifically designed and engineered for gynecological purposes including obstetrics. Infections, inflammations and cervical erosions are but a few of the conditions affecting the female reproductive system which could respond favorably to internal hydrotherapy at the discretion of the physician. By increasing the local blood supply through specific water temperature control, for example, it may be possible to produce a hyperemia to help overcome infections. The present concept can also be extended to include the slow gentle infusion of antibiotic or other medication directly to the membranes and localize foci of irritation. As an alternative to the conventional systemic or internal muscular infusion technique, use of the present apparatus can significantly contribute to the reduction of side effects or contra-indications to specific medications introduced orally or hypodermically. As a result, synergic reactions and symptoms can be kept at a minimum and side effects to both the digestive tract and the central nervous system can be reduced.

Therapeutical procedures utilizing the present apparatus may augment and enhance standard gynecological procedures and techniques. Biochemical balance and integrity are maintained in the physiological processes during therapy under proper utilization of water temperature, medication and vibratory stimulation. One possible application involves the introduction of a local anesthetic into the vagina prior to minor surgery. Furthermore, the combination of a cleansing action, asepsis and anesthetization in a multiple process would create a sterile field for surgical procedures and help eliminate complications. Thus, in providing an apparatus for successfully conducting the outlined therapeutic procedures, either in the maintenance of normalcy or in the correction of abnormalcy, there is created a valuable adjunct to orthodox gynecological and obstetrical procedures.

The internal hydrotherapy apparatus of the present invention is also designed for application to various genitourinary treatment procedures. By virtue of its design characteristics the apparatus provides a superior means for positioning a patient for catheterization procedures to withdraw urine. In a further application of the apparatus, a controlled gravitational flow of water or medicated solution introduced through the urethra by catheter may be utilized for the purpose of checking bacterial invasions of the urinary tract and providing anti-inflammatory and counter-irritation measures.

External lavage treatment may also be accomplished with the present apparatus as a result of the inclusion of a body wash spray system. Such lavage treatment may be carried out in conjunction with internal treatment utilizing the internal therapy aspects of the apparatus, or may be carried out in the absence of such internal treatment. Local external cleansing of the genital and rectal areas may readily be accomplished by the patient before, during or after such internal treatment, or alternatively after a bedridden patient has utilized the apparatus merely for the purpose of eliminating or defecating while confined to bed. In another aspect, inflammation of the external genitals, vulvitis and/or pruritus may respond favorably to cleansing measures administered with the present apparatus.

In a final aspect, the concept of a completely mobile and self-contained internal hydrotherapy unit offers the possibility of adaption to the rapidly expanding field of space medicine. For example, the concept may be embodied in a compact, personal and possibly disposable unit which might enjoy extensive success either in connection with space travel itself, or perhaps in connection with return or recovery procedures following such space travel.

BRIEF DESCRIPTION OF THE DRAWINGS

Referring now to the drawings.

DETAILED DESCRIPTION OF THE INVENTION

Figure 2:
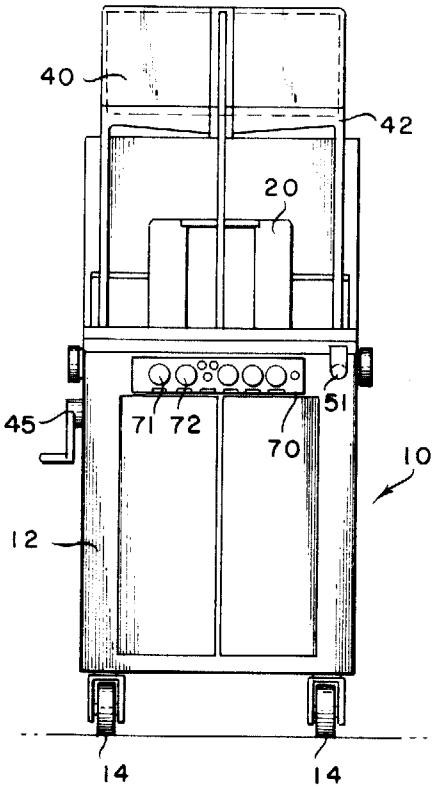
FIG. 2 is an end view of FIG. 1 taken from the front or foot of the apparatus.
Figure 1:
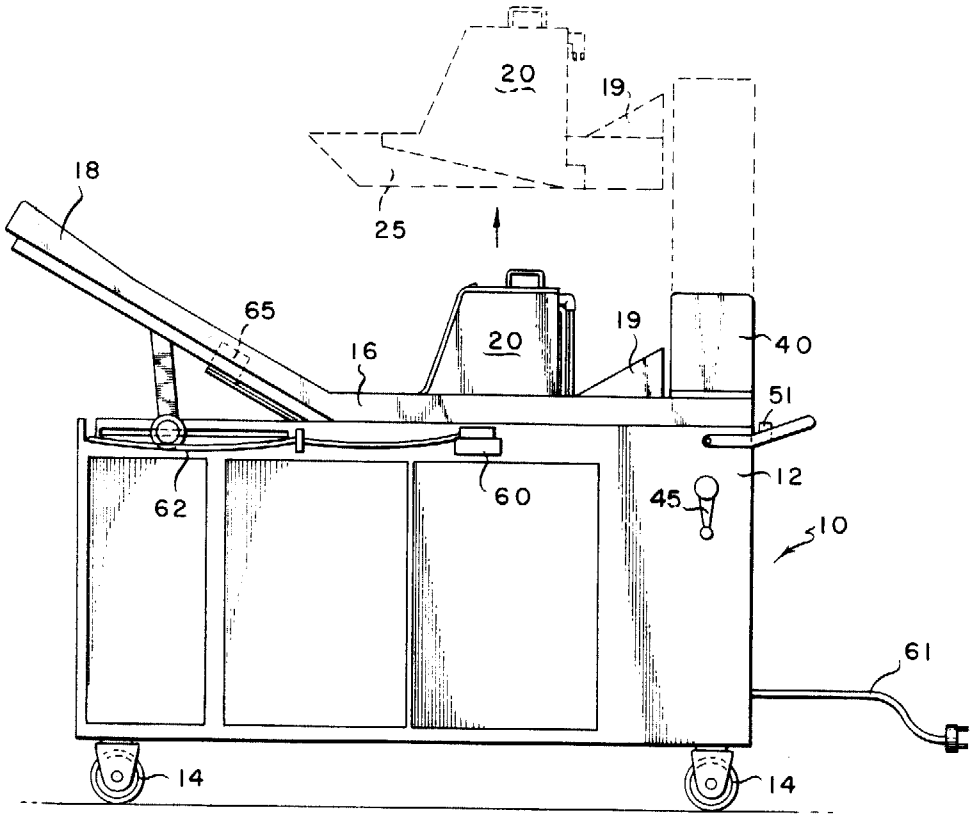
FIG. 1 represents a general overall side view of the internal hydrotherapy apparatus of the invention.

Referring to FIGS. 1 and 2 of the drawings, the internal hydrotherapy unit of the present invention, designated generally by reference numeral 10 in those figures, consists of a cabinet 12 made of suitable structural materials, and being of adequate size to contain the necessary equipment described below, and to permit a human patient to be positioned on its top surface in a reclining position for treatment. The cabinet is mounted on caster rollers 14 and is of general dimensions to facilitate moving it about the elevators, halls and rooms of a hospital, nursing home and similar establishments.

Figure 3:
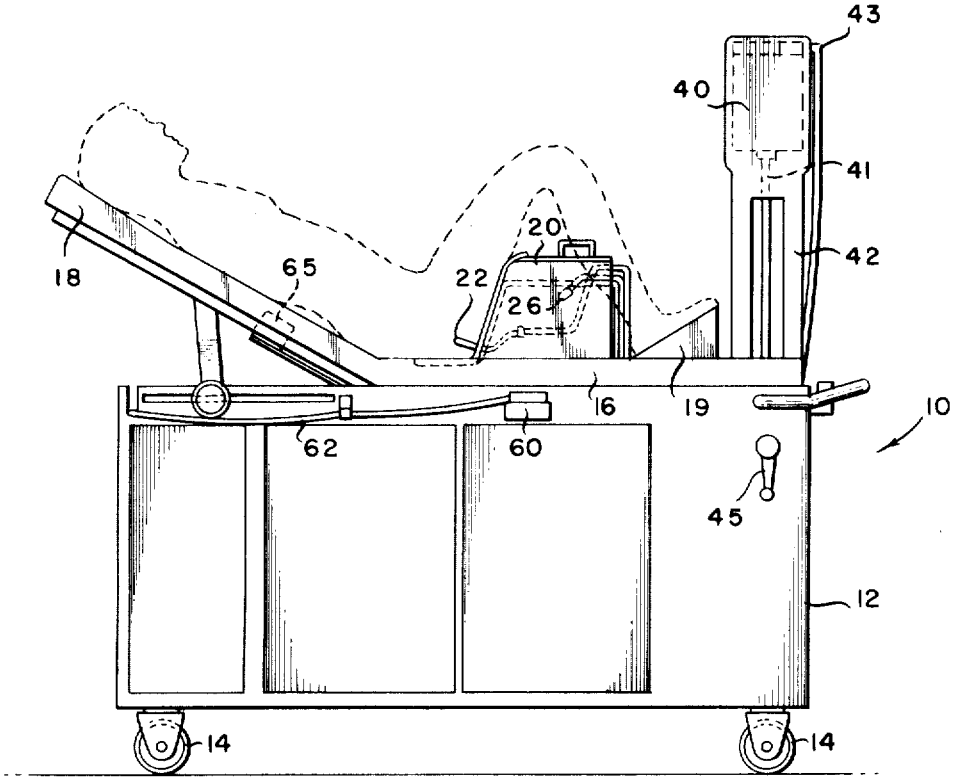
FIG. 3 is a part sectional part side view illustrating the treatment system in use with a patient being shown in phantom lines.

The top surface 16 of the cabinet is generally planar and of sufficient length to accommodate an adult patient. The surface may be padded, and is generally made of an easily cleanable material. The back portion 18 of the top surface of the cabinet is designed to support the trunk and head of the patient's body (as seen in FIG. 3) and is angularly adjustable from a horizontal position up through an angle of about 30°. The angular adjustment may be accomplished either by simple mechanical means or alternatively by provision of an electrically operated support system. Adjusting the cabinet top up in this way places the patient in a position similar to the natural squatting position for defecation, such a position being the most advantageous for internal hydrotherapy.

Occupying a position intermediate the adjustable back portion 18 of the cabinet top and the foot of the top surface is a treatment console 20. The console contains various treatment equipment as will be more fully discussed hereinafter. The dotted line exploded view representation of the console depicted at the top of FIG. 1 illustrates its overall configuration including a pair of foot rests 19 and a base portion 25, and further illustrates that the console is removable from the cabinet structure for placement on any auxiliary surface where it is desired to treat a patient.

The internal hydrotherapy apparatus of the present invention is comprised of four basic systems: a treatment system, a waste disposal system, a fresh water system and an electrical system. Each of these systems will be discussed separately below in connection with the appropriate drawings illustrating the various components of each.

THE TREATMENT SYSTEM

The component parts of the treatment system are best illustrated in FIG. 3 of the drawings. A treatment tank 40 is positioned on the cabinet top. The treatment tank consists of a suitable container typically having a capacity of at least about four gallons. The desired treating solution is contained in the tank for dispensation by gravity flow through a flexible hose or pipe 41 which carries the solution to the treatment area. The tank is mounted on a vertical track system 42 which enables the height of the tank to be adjusted to regulate the flow pressure to the treatment area. The tank elevation may be adjusted by any suitable gear or pulley means within the cabinet, and such means may be activated either by a hand crank 45 or alternatively by an electric motor. An auxiliary hose or pipe 43 enters the top of the treatment tank and provides for filling the tank with fresh water from the self-contained fresh water system embodied in the apparatus.

Figure 11:
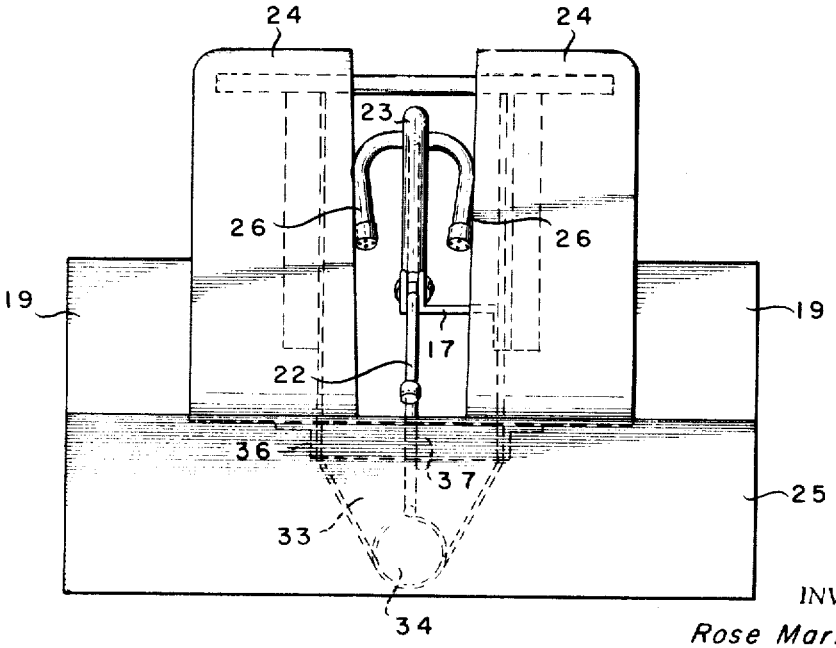
FIG. 11 is an end view taken from the front or right side of FIG. 9.
Figure 9:
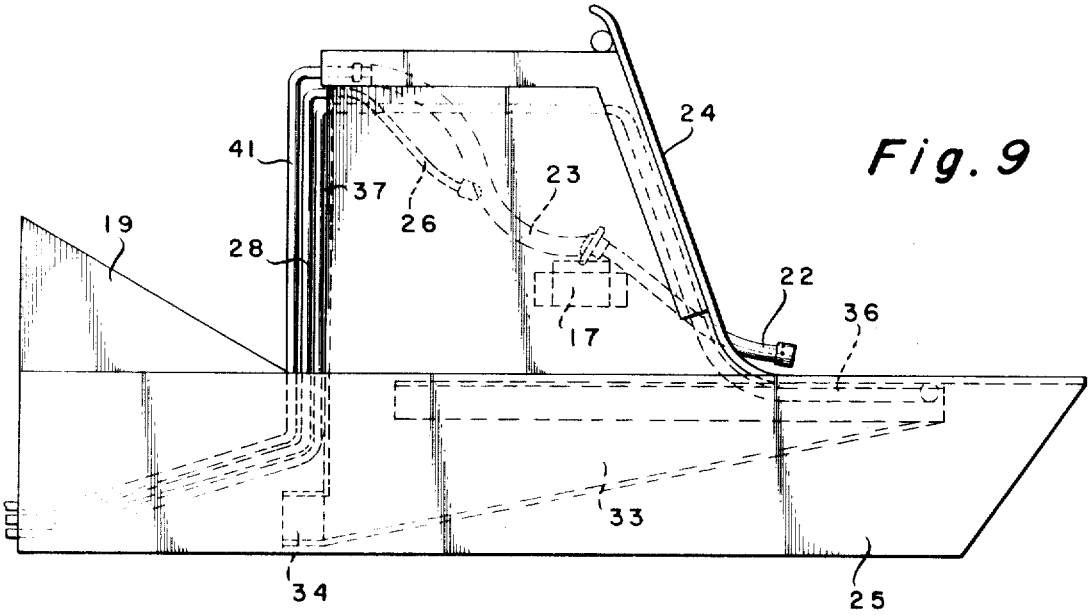
FIG. 9 is a side view of the treatment console, *with parts removed for the sake of clarity*.
Figure 10:
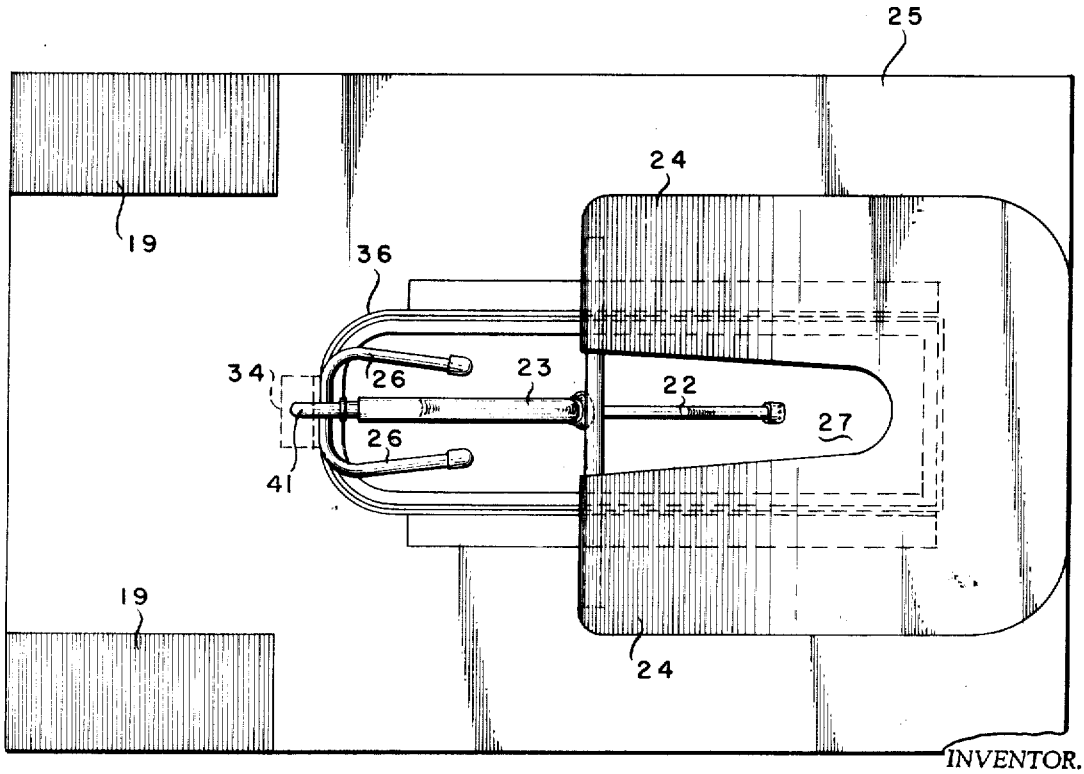
FIG. 10 is a top view of the FIG. 9 console.

The heart of the treatment system is embodied within the treatment console 20 which is illustrated in detail in FIGS. 9–11. The console contains a treatment nozzle 22 positioned in such a manner that when the patient is situated in a reclining position upon the cabinet top, with his knees upraised and his buttocks and upper thighs supported by the two horizontally spaced sloping surfaces 24 which define the rear face of the treatment console, the treatment nozzle will be positioned for insertion into the lower body orifices for infusion of solution from the treatment tank. The nozzle illustrated in FIGS. [11 and 12] *9–11* is a rectal nozzle, and is designed to follow and lie within the convolutions of the lumen of the anal canal and to allow the infiltration of gravity fed solution with no interference of evacuation function. The treatment nozzle is supplied with the treating solution through tube 23 and pipe 41 leading from the treatment tank 40.

The lavage system contained in the treatment console consists of body rinse nozzles 26 positioned in relation to and directed toward the opening 27 in the rear console face 24 and thus in position for directly cleansing the rectal and genital areas of the patient. The body spray nozzles are supplied through pipe 28 with fresh water from the self-contained fresh water system.

Each of the supply lines, 41 from the treatment tank to the treatment nozzle and 28 to the patient lavage system, contains a remote control flow regulating mechanism 58 (FIG. 6) such as a solenoid valve. Duplicate controls are provided for these valves, one set being placed on the master control panel 70 and the other on the patient's control panel 60. Most advantageously, these control systems are designed so that liquid flow continues only so long as the operator continues to depress the control button.

Referring now to FIG. 9, the preferred means for attaching the treatment nozzle 22 within the console 20 is illustrated by flexible hose section 23. The flexibility of this hose permits cooperation with an adjustment means 17 which allows the treatment nozzle to be placed in the proper position for treatment of the various lower orifices of the human body, and in addition provides for the treatment of both children and adults.

THE WASTE DISPOSAL SYSTEM

Figure 5:
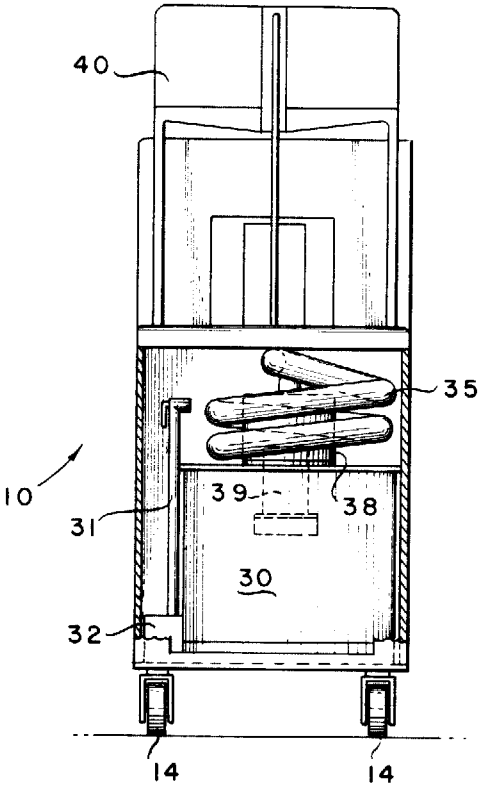
FIG. 5 is a right end view of the FIG. 4 apparatus.
Figure 4:
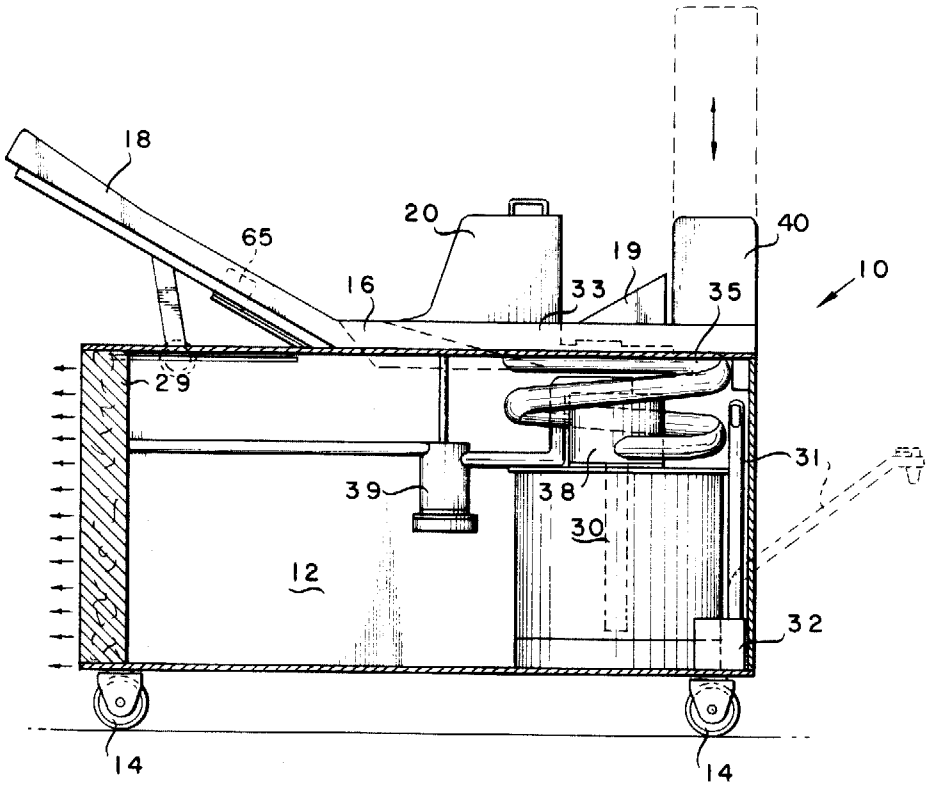
FIG. 4 is a part sectional part side view with parts removed for the sake of clarity illustrating the elements of the waste disposal system.

The elements of the waste disposal system are best shown in FIGS. 4 and 5 of the drawings. In the lower portion of the cabinet there is positioned a waste collection tank 30 which provides for the ultimate collection of any solid and liquid waste and spent treating solution resulting from the treatment. Attached to the waste tank is a flexible hose 31 which provides a means to empty the contents of the waste tank into any conventional sewer or water disposal system. Emptying may be provided by any suitable means as for example a non-clog waste pump 32. Initial collection of any waste material and spent treating solution as it is discharged from the patient's body is achieved by means of the treatment receptacle 33 which is located in the lower portion of the treatment console 20. The treatment receptacle comprises a sloping pan arrangement (FIGS. 9–11) positioned immediately beneath the treatment area, and designed to empty through opening 34 located in the lower forward portion of the treatment console. The waste material collected in the treatment receptacle is discharged through opening 34 to a suitable flexible hose 35 through which it is carried ultimately to the waste collection tank 30.

To facilitate removal of waste material from the treatment receptacle 33, the area immediately above and surrounding the receptacle may be provided with a flush ring such as that identified in FIGS. 9 and 10 by reference numeral 36. The flush ring, concentric with the treatment receptacle, is supplied with fresh water through line 37 from the fresh water supply system, and provides a means to flush all waste material from the treatment area as desired by the patient or operator. Suitable control means such as a solenoid valve may be located in line 37 and its operation controlled from either of the two control panels 60 and 70.

Referring again to FIG. 4, the waste disposal system may additionally embody a means for separating any entrained air from the solid and liquid wastes sought to be disposed of. Such a means is represented by the cyclone separator designated by reference numeral 38. The solid and liquid waste are discharged from the separator means to the waste collection tank 30, while the air is led off through suitable vacuum pump means 39, and further through odor absorbing filters 29 to be discharged to the atmosphere.

The control panel 70 depicted in FIG. 2 contains two gauges relating to the waste disposal system. These gauges 71 and 72 record the level of liquid and solid waste present in the waste collection tank, and the vacuum pressure maintained in the air purification system by the vacuum pump 39.

THE FRESH WATER SYSTEM

Figure 7:
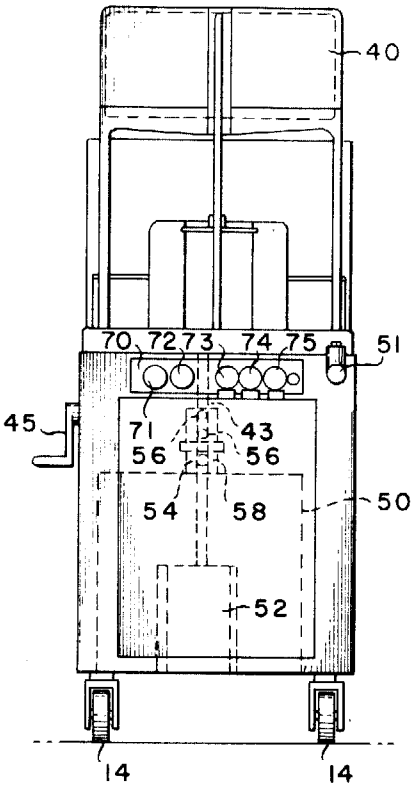
FIG. 7 is a right end view of the FIG. 6 apparatus.
Figure 6:
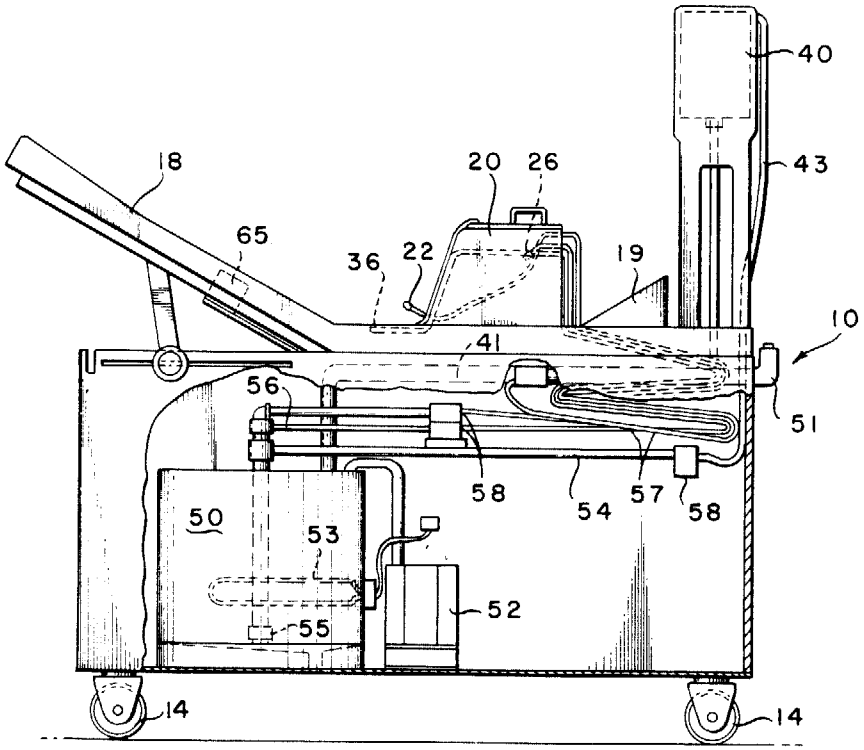
FIG. 6 is a part sectional part side view of the apparatus, with parts removed for the sake of clarity illustrating the elements of the fresh water system.

FIGS. 6 and 7 illustrate the elements of the fresh water system contained in the present internal hydrotherapy apparatus. The primary element is the fresh water storage tank 50 which is located in the base portion of the cabinet. The tank is filled through a normally capped pipe 51 which extends from the tank to any accessible location on the exterior of the cabinet wall. In order to dispense water from the storage tank to the treatment system and waste disposal system, the storage tank is provided with a suitable pump 52 which supplies the pressure necessary for such distribution.

It has been found desirable to control the temperature of the water to be used for internal therapy and patient lavage treatment, and consequently means are provided for controlling the temperature of the water in the storage tank. Typical means are illustrated in the form of an electric induction coil 53 which protrudes into the interior of the water storage tank and allows the water therein to be heated to any desirable level above ambient temperature. Such an induction heating device may be controlled with any standard thermostat equipment, which in turn, may advantageously have its settings regulated by either or both control panels.

Several sets of pipes are provided for distributing the water from the storage tank to the treatment and waste disposal systems. Fresh water is supplied to the treatment tank 40 through a combination of pipe 54 and flexible hose 43. Additional pipes 56 lead to other flexible hoses 57 which supply fresh water to the patient lavage system 26 and the waste flush ring 36, both located in the treatment console 20. Each fresh water line contains a solenoid valve 58, or other type remote control valve, so that the flow of water through said lines can be controlled either by the patient or by the operator from either of the two control panels. All fresh water utilized in the present apparatus is filtered before distribution from the water storage tank by filter 55 positioned in the main discharge pipe. Gauges 73, 74 and 75 on control panel 70 in FIG. 4 monitor the volume or level of water in the fresh water storage tank, the temperature of the water and the pressure maintained in the fresh water system.

THE ELECTRICAL SYSTEM

The electrical system consists generally of a heavy duty extension cord 61 fitted with a plug, the necessary electrical equipment, e.g., pumps, solenoid valves, separator, guages, lights, etc., and suitable wiring to provide electric current to the electrical equipment. It has also been found desirable to incorporate an electric vibrating device into the design of the present apparatus. Such a device, designated by reference numeral 65 in FIG. 3, is conveniently and appropriately positioned in the angularly adjustable portion 18 of the cabinet surface which is designed to support the trunk portion of the patient's body. In this position the maximum possible relaxation benefit will be achieved by the patient.

The on-off switch controls for all of the electrically operated equipment as well as the indicating gauges for the various systems are contained on the operator's control panel 70. Optionally, warning lights may be placed on the control panel to indicate that the pump switches and/or heater switch are in the "on" position and also to indicate low level of the fresh water storage tank as well as high level in the waste collection tank. Duplicate control switches for the valves to the internal treatment nozzle, the patient lavage, the waste flush ring and the vibrator are contained in a hand control unit 60 (FIG. 1) mounted on a flexible cable 62 and available to the person being treated. In addition, it has been found desirable to equip the control valves on the fresh water supply lines to the patient lavage and flush ring with automatic reset timers that limit the "on" time to a few seconds and do not reset for a similar period of time, e.g., the time may be adjustable in a range of 5 to 15 seconds.

TREATMENT WITH REMOVABLE CONSOLE

Figure 8:
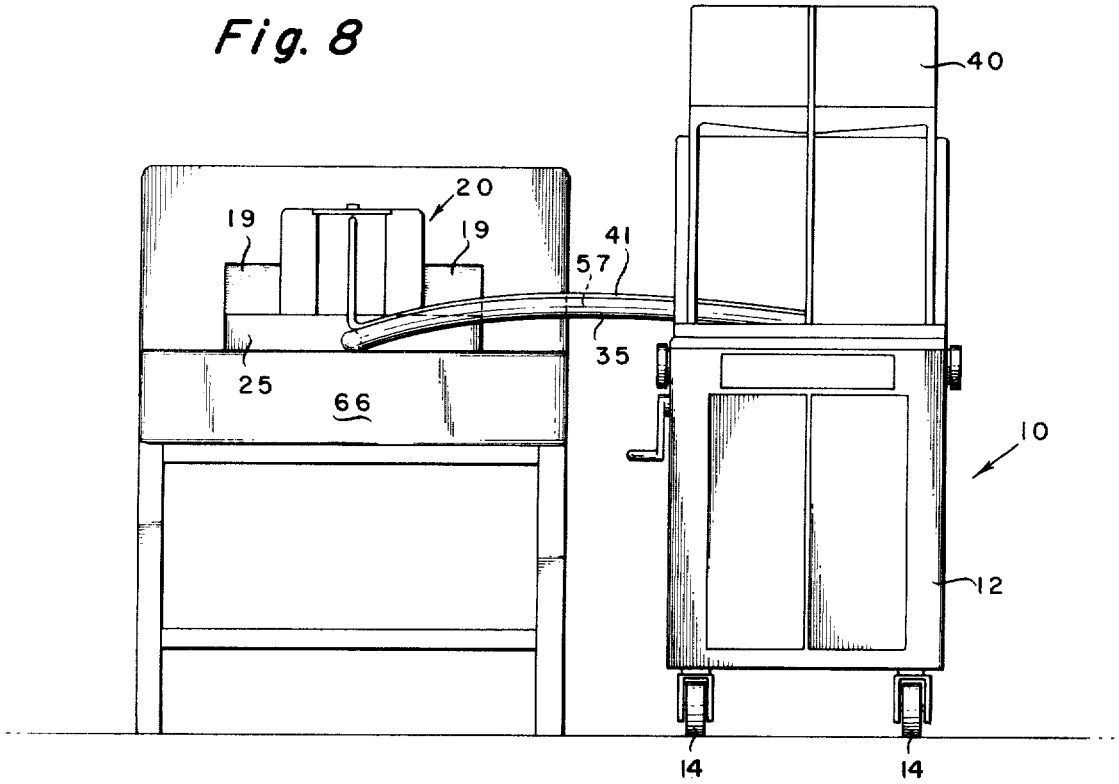
FIG. 8 is an end view of the apparatus having its treatment console removed and placed on a hospital bed.

A further feature of the internal hydrotherapy apparatus of the present invention is illustrated in FIG. 8 of the drawings. In this view the console 20 and its attachments, e.g., foot rests 19, are mounted on a removable segment 25 of the cabinet top, and all connections from the cabinet to the console are via the previously described flexible hoses 35, 41 and 57. It will be understood that the hoses are of sufficient length when uncoiled to enable the console to be removed as shown. This removable feature likewise prompted connection of the patient's control box 60 in FIG. 1 through flexible cable 62 so that exclusive patient control of the treatment apparatus would also be available to bedridden patients.

The apparatus in its auxiliary removed position is used in connection with any bed 66, however, it is preferable that a standard adjustable hospital bed be employed since it would provide for the angular adjustment of the patient's trunk portion so as to enable the patient to assume a natural position for internal treatment.

The removable segment 25 of the cabinet top upon which the console 20 is mounted is pictured in detail in FIGS. 9 and 10 of the drawings. The segment is generally from about 2 to 3 feet in length, from about 1 to 2 feet in width and several inches in thickness. It extends several inches in length beyond the console itself to include the foot rests 19 which are desirable for proper treatment even when the apparatus is being used in conjunction with a bedridden patient. The portion of the removable segment 25 of the counter top which surrounds the console and forms the base of the removable segment is typically manufactured from a light material having cushioning properties such as foamed polystyrene, polyurethane, rubber or other synthetic material.

The foregoing description of the present internal hydrotherapy apparatus has been made in terms of a limited number of embodiments, and it is quite apparent that many and varied embodiments of the present invention may readily suggest themselves to one of ordinary skill in the art upon being advised of the present invention. For example, many alternative designs for the body support members may be employed in the present invention, and various different arrangements of the treatment elements and systems may be substituted for the equivalent configurations herein disclosed. In this context, it is to be understood that the disclosure is intended to be merely illustrative, and no way limitative, the invention being defined and delimited only by the scope of the appended claims.

What is claimed is:

1. A self-contained internal hydrotherapy apparatus comprising a mobile cabinet having a top surface designed to accommodate a human patient's body in reclining position with the knees upraised, said surface having a portion designed to support the trunk and head of said patient's body and being angularly adjustable from horizontal through an angle of about 30°, a removable treatment console located on the top surface of the cabinet proximate to said angularly adjustable portion of said surface, said console having two horizontally spaced surfaces designed to support the buttocks and upper thighs of a reclining patient, said console being contained on a detachable segment of the cabinet surface which is removable from the cabinet top for placement on an auxiliary surface whereupon treatment of a patient is desired, said cabinet further containing (a) a patient treatment system comprising a treatment tank mounted above the top surface of the cabinet and being vertically adjustable with relation to said cabinet, a treatment nozzle positioned in the console for insertion into the orifices of the patient's lower body for infusion of solution from said treatment tank, and flexible connective conduit means for fluid flow between said tank and said treatment nozzle, and (b) a waste disposal system comprising a waste collection tank positioned inside the cabinet, a treatment receptacle located in the lower portion of the treatment console to collect waste discharged from the patient during treatment and flexible connective conduit means between said treatment receptacle and said waste collection tank, said flexible connective conduit means for fluid flow between said tank and said treatment nozzle and said flexible connective conduit means between said treatment receptacle and said waste collection tank each having excess length normally stored in said cabinet sufficient to allow both conduit means to be extended to permit removal of the console from the cabinet and placement upon the auxiliary surface.

2. An internal hydrotherapy apparatus according to claim 1 further comprising lavage means positioned in said console to wash the rectal and genital areas of the patient's body.

3. An internal hydrotherapy apparatus according to claim 2, further comprising a self contained fresh water system, and means to flush collected waste material from said treatment receptacle to said waste collection tank with fresh water, from said fresh water system.

4. An internal hydrotherapy apparatus according to claim 3, further comprising means positioned between the treatment receptacle and the waste collection tank to separate air from solid and liquid waste material collected in said treatment receptacle, and means to deodorize said separated air and discharge the deodorized air into the atmosphere.

5. An internal hydrotherapy apparatus according to claim 4 further comprising means to control the temperature of the water stored in said water storage tank, and remote control means to regulate the flow of water from said storage tank to the said lavage means, said flushing means and to said treatment tank.

6. An internal hydrotherapy apparatus according to claim 5 further comprising an electrical vibrator contiguous with the body trunk support portion of said cabinet top.

7. An internal hydrotherapy apparatus according to claim 3 further comprising remote control means to regulate the flow of fresh water between said storage tank and said lavage means, said flush means, and said treatment tank, and remote control means to regulate the flow of treating solution from said treatment tank to said treatment nozzle, each of said control means being attached to the apparatus by a flexible cable of sufficient length to allow use of the control means by a patient being treated by the apparatus on an auxiliary surface.

*8. A self-contained internal hydrotherapy apparatus comprising a mobile cabinet, a removable treatment console located on the top surface of the cabinet, said console having two horizontally spaced surfaces designed to support the buttocks and upper thighs of a reclining patient, said console being removable from the cabinet top for placement on an auxiliary surface whereupon treatment of a patient is desired, said cabinet comprising*

*(a) a patient treatment system comprising a treatment tank for holding a solution for use in treating a patient, a treatment nozzle positioned in the console for insertion into the orifices of the patient's lower body for infusion of solution from said treatment tank, and flexible connective conduit means for fluid flow between said tank and said treatment nozzle, and*

*(b) a waste disposal system comprising a waste collection tank positioned inside the cabinet, a treatment receptacle located in the lower portion of the treatment console to collect waste discharged from the patient during treatment, and flexible connective conduit means between said treatment receptacle and said waste collection tank, said flexible connective conduit means for fluid flow between said tank and said treatment nozzle and said flexible connective conduit means between said treatment receptacle and said waste collection tank each having a length sufficient to allow both conduit means to be extended to permit removal of the console from the cabinet and placement upon the auxiliary surface.*

*9. An internal hydrotherapy apparatus according to Claim 8, further comprising a self-contained fresh water system, and means to flush collected waste material from said treatment receptacle to said waste collection tank with fresh water, from said fresh water system.*

*10. An internal hydrotherapy apparatus according to Claim 9, further comprising remote control means to regulate the flow of fresh water between said storage tank and said lavage means, said flush means, and said treatment tank, and remote control means to regulate the flow of treating solution from said treatment tank to said treatment nozzle, each of said control means being attached to the apparatus by a flexible cable of sufficient length to allow use of the control means by a patient being treated by the apparatus on an auxiliary surface.*

References Cited

The following references, cited by the Examiner, are of record in the patented file of this patent or the original patient.

UNITED STATES PATENTS

| | | | |
|---|---|---|---|
| 2,506,183 | 5/1950 | Touchberry | 128—227 X |
| 2,818,862 | 1/1958 | Wanek | 128—227 |
| 2,328,893 | 9/1943 | Conrad | 128—230 X |
| 2,252,569 | 8/1941 | Kennison | 128—227 |
| 1,945,081 | 1/1934 | Ryan et al. | 128—227 X |
| 2,564,135 | 8/1951 | Touchberry | 269—327 |
| 3,401,694 | 9/1968 | Touchberry | 128—227 |
| 1,758,332 | 5/1930 | Pittam et al. | 128—227 |

FOREIGN PATENTS

| | | | |
|---|---|---|---|
| 242,460 | 4/1947 | Switzerland | 128—227 |
| 634,229 | 4/1927 | France | 128—227 |
| 777,935 | 3/1935 | France | 128—227 |
| 138,801 | 6/1933 | Austria | 128—227 |

RICHARD A. GAUDET, Primary Examiner

J. YASKO, Assistant Examiner

U.S. Cl. X.R.

4—174, 222; 128—33; 269—327